(12) United States Patent
Srinivasan et al.

(10) Patent No.: US 12,704,497 B2
(45) Date of Patent: Aug. 11, 2026

(54) ANALYSIS OF SOURCE ROCKS IN PYROLYSIS EXPERIMENTS

(71) Applicant: Saudi Arabian Oil Company, Dhahran (SA)

(72) Inventors: Poorna Srinivasan, Houston, TX (US); Estefania M. Endara Arguello, Brookshire, TX (US); Shannon L. Eichmann, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 349 days.

(21) Appl. No.: 18/591,635

(22) Filed: Feb. 29, 2024

(65) Prior Publication Data

US 2025/0277765 A1 Sep. 4, 2025

(51) Int. Cl.
*G01N 33/24* (2006.01)
*G01N 1/28* (2006.01)
(Continued)

(52) U.S. Cl.
CPC .......... *G01N 33/241* (2013.01); *G01N 1/286* (2013.01); *G01N 23/2251* (2013.01);
(Continued)

(58) Field of Classification Search
CPC ...... G01N 33/24; G01N 33/241; G01N 1/286; G01N 23/2251; G01N 25/145;
(Continued)

(56) References Cited

U.S. PATENT DOCUMENTS 3,456,183 A 7/1969 Codrington et al.
3,834,122 A 9/1974 Allison et al.
(Continued)

FOREIGN PATENT DOCUMENTS

AU 2012359291 7/2013
AU 2021250869 7/2022
(Continued)

OTHER PUBLICATIONS

Alhammadi et al., "Pore-scale Imaging and Characterization of Hydrocarbon Reservoir Rock Wettability at Subsurface Conditions Using X-ray Microtomography," Journal of Visualized Experiments, Oct. 2018, 140:1-15, 15 pages.
(Continued)

*Primary Examiner* — Benjamin R Schmitt
(74) *Attorney, Agent, or Firm* — Fish & Richardson P.C.

(57) ABSTRACT

The apparatus includes a pyrolysis chamber configured to receive and hold within an interior space a volume of an aqueous fluid and to maintain a pressure within the interior space for a duration of an experimental period when a removable head is in a closed position. The apparatus includes a sample basket assembly comprising a plurality of baskets attached to the removable head by one or more rods. Each basket is configured to receive one or more source rock samples. The sample basket assembly is configured such that, when the removable head is in the closed position and the one or more source samples are disposed within each basket, the samples suspended in a substantially stationary position above the floor.

20 Claims, 5 Drawing Sheets

(51) Int. Cl.
*G01N 23/2251* (2018.01)
*G01N 25/14* (2006.01)
*G01N 30/12* (2006.01)
*G01N 30/88* (2006.01)
*E21B 49/00* (2006.01)

(52) U.S. Cl.
CPC .......... *G01N 25/145* (2013.01); *G01N 30/12* (2013.01); *G01N 30/88* (2013.01); *E21B 49/00* (2013.01); *G01N 2001/2873* (2013.01); *G01N 2030/125* (2013.01); *G01N 2030/8854* (2013.01)

(58) Field of Classification Search
CPC .................. G01N 30/12; G01N 30/88; G01N 2001/2873; G01N 2030/125; G01N 2030/8854; E21B 49/00
See application file for complete search history.

(56) References Cited

U.S. PATENT DOCUMENTS 4,344,917 A 8/1982 Schorno
4,485,071 A 11/1984 Larter
4,842,825 A 6/1989 Martin
4,882,128 A 11/1989 Hukvari et al.
5,180,556 A 1/1993 Nolte et al.
5,390,529 A 2/1995 Ghiselli
5,441,343 A 8/1995 Pylkki et al.
6,095,679 A 8/2000 Hammiche et al.
6,411,902 B1 6/2002 Wiltshire
6,440,746 B1 * 8/2002 Troxler .................. G01N 31/12 436/139
6,491,425 B1 12/2002 Hammiche et al.
6,590,647 B2 7/2003 Stephenson
6,706,531 B1 * 3/2004 Haeseler .............. G01N 33/241 436/139
7,078,237 B1 7/2006 Mowry
7,086,484 B2 8/2006 Smith
7,588,827 B2 9/2009 Nie et al.
7,879,625 B1 2/2011 Boss
7,983,845 B2 7/2011 Minh
8,177,422 B2 5/2012 Kjoller et al.
8,278,931 B2 10/2012 Fang et al.
8,337,783 B2 12/2012 Locascio et al.
8,473,213 B2 6/2013 Zhu et al.
8,729,903 B2 5/2014 Srnka et al.
8,818,778 B2 8/2014 Salazar-Tio et al.
8,821,806 B2 9/2014 Hersherwitz et al.
9,029,156 B2 5/2015 Kornacki et al.
9,057,797 B2 6/2015 Omeragic et al.
9,128,210 B2 9/2015 Pomerantz
9,152,745 B2 10/2015 Glinsky
9,274,324 B2 3/2016 Kurioka et al.
9,507,047 B1 11/2016 Dvorkin et al.
9,696,270 B1 7/2017 Roy et al.
9,784,882 B2 10/2017 Vinegar et al.
9,995,698 B2 6/2018 Suarez-Rivera et al.
10,012,765 B2 7/2018 Haas et al.
10,043,274 B2 8/2018 Varslot et al.
10,198,804 B2 2/2019 Sungkorn et al.
10,422,736 B2 9/2019 Walls et al.
10,611,967 B2 4/2020 Inan
10,816,452 B2 10/2020 Wang et al.
11,268,919 B2 3/2022 Eichmann et al.
11,352,879 B2 6/2022 Li et al.
2008/0110253 A1 5/2008 Stephenson et al.
2008/0111064 A1 5/2008 Andrews et al.
2009/0187391 A1 7/2009 Wendt et al.
2010/0092865 A1 4/2010 Kanno et al.
2010/0224823 A1 9/2010 Yin et al.
2011/0207231 A1 8/2011 Natan et al.
2011/0260051 A1 10/2011 Preudhomme et al.
2011/0275061 A1 11/2011 Weidemaier et al.
2012/0026037 A1 2/2012 Thomson et al.
2012/0257199 A1 10/2012 Liu et al.
2012/0273193 A1 11/2012 Sen
2012/0281883 A1 11/2012 Hurley et al.
2013/0013209 A1 1/2013 Zhu et al.
2013/0040292 A1 2/2013 Lopez et al.
2013/0084643 A1 4/2013 Commarieu et al.
2013/0238304 A1 9/2013 Glinsky
2013/0259190 A1 10/2013 Walls et al.
2013/0259808 A1 10/2013 Chen et al.
2013/0341028 A1 12/2013 Christian et al.
2014/0048694 A1 2/2014 Pomerantz
2014/0052420 A1 2/2014 Cavanaugh
2014/0077121 A1 3/2014 Sun et al.
2014/0186939 A1 7/2014 Peterman et al.
2014/0360973 A1 12/2014 Yin et al.
2015/0038347 A1 2/2015 Johnson et al.
2015/0079270 A1 3/2015 Wang et al.
2015/0168588 A1 6/2015 Vinegar et al.
2016/0017202 A1 1/2016 Yang et al.
2016/0341707 A1 11/2016 Inan
2017/0059497 A1 3/2017 Seltzer
2017/0067836 A1 3/2017 Hull et al.
2017/0336528 A1 11/2017 Badri et al.
2018/0134964 A1 5/2018 Inan
2019/0118265 A1 4/2019 Nie et al.
2020/0231878 A1 * 7/2020 Inan ...................... G01N 1/286
2021/0080413 A1 3/2021 Eichmann et al.
2021/0080414 A1 3/2021 Eichmann et al.
2022/0205880 A1 6/2022 Wang et al.
2022/0228997 A1 7/2022 Sandu et al.
2022/0317015 A1 10/2022 Sun et al.
2023/0408429 A1 12/2023 Eichmann

FOREIGN PATENT DOCUMENTS

CN 87213495 6/1988
CN 203785967 8/2014
CN 105784628 7/2016
CN 106525898 3/2017
CN 108152145 6/2018
CN 111380893 7/2020
CN 111504759 A * 8/2020 ............... G01N 1/42
EP 0210845 2/1987
EP 0247669 12/1987
EP 2040075 3/2009
EP 4028780 3/2021
GB 2161269 8/1988
KR 101384986 4/2014
WO WO 2010019256 2/2010
WO WO 2014008496 1/2014
WO WO 2014014919 1/2014
WO WO 2015058206 4/2015
WO WO 2016087397 6/2016
WO WO 2017164822 9/2017
WO WO 2018170035 9/2018
WO WO 2020009981 1/2020
WO WO 2022159542 7/2022
WO WO 2022187600 9/2022

OTHER PUBLICATIONS

Andra et al., "Digital rock physics benchmarks—Part I: Imaging and segmentation," Computers & Geosciences, Jan. 2013, 50:25-32, 8 pages.
Andra et al., "Digital rock physics benchmarks—Part II: Computing effective properties," Computers & Geosciences, Jan. 2013, 50:33-43, 11 pages.
Arns et al., "Pore Scale Characterisation of Carbonates using X-ray microtomography," Paper presented at the SPE Annual Technical Conference and Exhibition, Sep. 26-29, 2004, 11 pages.
Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 2017, 170:390-397, 8 pages.
Biot et al., "Temperature analysis in hydraulic fracturing," Journal of Petroleum Technology, Nov. 1987, 39(11):1389-1397, 9 pages.

(56) References Cited

OTHER PUBLICATIONS

Blanz et al., "Nuclear Magnetic Resonance Logging While Drilling (NMR-LWD): From an Experiment to a Day-to-Day Service for the Oil Industry," Diffusion Fundamentals, 2010, 14(2), 5 pages.
Bultreys et al., "Imaging and image-based fluid transport modeling at the pore scale in geological materials: A practical introduction to the current state-of-the-art," Earth-Science Reviews, Apr. 2016, 155:93-128, 36 pages.
Cahill et al., "Nanoscale thermal transport," Journal of Applied Physics, Jan. 15, 2003, 93(2):793-818, 27 pages.
Cahill et al., "Nanoscale Thermal Transport. II. 2003-2012," Applied Physics Reviews, 2014, 1(011305):1-46, 46 pages.
Capsan et al., "Using core data, digital rocks, and source rock kinetics to reduce hydrocarbon storage uncertainty in unconventional reservoirs: application to south Texas organic rich mudstones," presented at the Unconventional Resources Technology Conference, San Antonio, Texas, Aug. 1-3, 2016, 20 pages.
Clough et al., "Characterization of Kerogen and Source Rock Maturation Using Solid-State NMR Spectroscopy," Energy & Fuels, Sep. 15, 2015, 29(10):6370-6382, 42 pages.
Cnudde et al., "High-resolution X-ray computed tomography in geosciences: A review of the current technology and applications," Earth-Science Reviews, Aug. 1, 2013, 123: 1-17, 17 pages.
Dandy, "Supercritical Fluids and their Application to the Recycling of High-Performance Carbon Fibre Reinforced Composite Materials," thesis submitted for the degree of Doctor of Philosophy, University of Birmingham, Apr. 2015, 314 pages.
Dawson et al., "Geochemical and geomechanical testing of near wellbore CO2 injectivity improvement," ANLEC Project 7-1110-0101, Oct. 2014, 146 pages.
Deng et al., "Evaluation of high-temperature deformation of porous asphalt mixtures based on microstructure using X-ray computed tomography," Construction and Building Materials, Dec. 10, 2019, 227(116623):1-10, 10 pages.
Ducros, "Source Rock Kinetics: Goal and Perspectives," Source Rock Kinetics: Goal and Perspectives. AAPG Geosciences Technology Workshop, Jul. 5, 2016, 30 pages.
Eichmann et al. "Improved Nanoscale Image-based Reservoir Characterization using Supervised Machine Learning," Unconventional Resources Technology Conference, OnePetro, 2021, 14 pages.
Eichmann et al., "Quantitative Image Analysis of Source Rocks Using Machine Learning Segmentation," Microscopy and Microanalysis, 2020, 26(S2):2862-2865, 4 pages.
Esfahani et al., "Quantitative nanoscale mapping of three-phase thermal conductivities in filled skutterudites via scanning thermal microscopy," National Science Review, Jun. 30, 2017, 5(1):59-69, 11 pages.
Espitalie et al., "Source rock characterization method for petroleum exploration," OTC-2935-MS, presented at the Offshore Technology Conference, Houston, Texas, May 2-5, 1977, 6 pages.
Gao et al., "A Surface Functional Monomer-Directing Strategy for Highly Dense Imprinting of TNT at Surface of Silica Nanoparticles," Journal of American Chemical Society, Jun. 6, 2007, 129(25):7859-7866, 8 pages.
Glatz et al., "An experimental platform for triaxial high-pressure/high-temperature testing of rocks using computed tomography," Review of Scientific Instruments, Apr. 5, 2018, 89(045101):1-10, 10 pages.
Glossary.oilfield.slb.com [online] "Dean-Stark extraction," Sclumberger Oilfield Glossary, retrieved on May 3, 2022, retrieved from URL, <https://glossary.oilfield.slb.com/en/terms/d/dean-stark extraction>, 2 pages.
Glossary.oilfield.slb.com [online] "distillation extraction," Sclumberger Oilfield Glossary, retrieved on May 3, 2022, retrieved from URL, <https://glossary.oilfield.slb.com/en/terms/d/distillation_extraction>, 2 pages.
Goethals et al., "Comparison of Positron Emission Tomography and X-ray radiography for studies of physical processes in sandstone," Engineering Geology, Feb. 10, 2009, 103(3-4):134-138, 5 pages.
Hirono et al., "Porosity profile within the Taiwan Chelungpu Fault, reconstructed from X-ray computed tomography images," JAMSTEC Report of Research and Development, Sep. 2009, 9(2):15-22, 8 pages.
Hu et al., "Smart Liquid SERS Substrates based on Fe3O4/Au Nanoparticles with Reversibly Tunable Enhancement Factor for Practical Quantitative Detection," Scientific Report, Nov. 27, 2014, 4(7204), 10 pages.
Huang et al., "A new pyrolysis technique using a diamond anvil cell: in situ visualization of kerogen transformation," Organic Chemistry, Jan. 1996, 24(1):95-107, 13 pages.
Hull et al., "New Frontiers in Oil and Gas Exploration," Chapter 10: Insights of the Rev of Source Shale from Nano- and Micromechanics, Springer International Publishing Switzerland, 2016, 32 pages.
Iglauer et al., "High pressure-elevated temperature x-ray micro-computed tomography for subsurface applications," Advances in Colloid and Interface Science, Jun. 2018, 256:393-410, 18 pages.
Iovea et al., "Dual-energy X-ray computer axial tomography and digital radiography investigation of cores and other objects of geological interest," Engineering Geology, Feb. 10, 2009, 103(3-4):119-126, 8 pages.
Jacobs et al., "'Applications of X-ray computed tomography in engineering geology' or 'looking inside rocks . . . '," Engineering Geology, Feb. 10, 2009, 103(3-4):67-68, 2 pages.
Kim et al., "Permeability and Porosity Evolution of Organic Rich Shales as a Result of Heating, " Paper presented at the SPE Western Regional Meeting, Apr. 22, 2019, 43 pages.
Kim et al., "Permeability and Porosity Evolution of Organic-Rich Shales from the Green River Formation as a Result of Maturation," SPE-195366-PA, Jun. 11, 2020, 25(3):1377-1405, 29 pages.
Klapetek, "Chapter 11: Thermal Measurements," Quantitative Data Processing in Scanning Probe Microscopy: SPE Applications for Nanometrology, 2018, 26 pages.
Kobchenko et al., "4D imaging of fracturing in organic-rich shales during heating," Journal of Geophysical Research, Dec. 7, 2011, 116(B12201):1-9, 9 pages.
Lewan et al., "Comparison of petroleum generation kinetics by isothermal hydrous and nonisothermal open-system pyrolysis," Organic Geochemistry, 2002, 33:1457-1475, 19 pages.
Lewan et al., "Oil-generation kinetics for organic facies with Type-II and -IIS kerogen in the Menilite Shales of the Polish Carpathians," Geochimica et Cosmochimia Acta, Apr. 2006, 70:3351-3368, 18 pages.
Lewan, "Evaluation of petroleum generation by hydrous pyrolysis experimentation," Phil. Trans. R. Soc. Lond. A, 1985, 315:123-134, 12 pages.
Lewan, "Experiments on the role of water in petroleum formation," Geochimica et Cosmochimica Acta, 1997, 61(17):3691-3723, 33 pages.
Lewan, "Laboratory simulation of petroleum formation: hydrous pyrolysis," Organic Geochemistry, 1993, 419-442, 25 pages.
Little et al., "Correlating oils in Turonian-Cenomanian source rocks using hydrous pyrolysis and organic sulfur compounds," AAPG Search and Discovery Article, Oct. 2012, 10453:1-40, 40 pages.
Lu et al., "Quantitative prediction of seismic rock physics of hybrid tight oil reservoirs of the Permian Lucaogou Formation, Junggar Basin, Northwest China," Journal of Asian Earth Sciences, 2019, 178:216-223, 8 pages.
Luffel et al., "New core analysis methods for measuring reservoir rock properties of Devonian Shale," Journal of Petroleum Technology, Nov. 1992, 44(11):1184, 7 pages.
Mao et al., "Chemical and nanometer-scale structure of kerogen and its change during thermal maturation investigated by advanced solid-state 13C NMR spectroscopy," Geochimica et Cosmochimica Acta, 2010, 74(7):2110-2127, 18 pages.
Matthews et al., "A review of the application of X-ray computed tomography to the study of coal," Fuel, Dec. 1, 2017, 209:10-24, 15 pages.
McCarthy et al., "Basic petroleum geochemistry for source rock evaluation," Oilfield Review, 2011, 23(2), 32-43, 12 pages.

(56) References Cited

OTHER PUBLICATIONS

Meyer et al., "Identification of Source Rocks on Wireline Logs by Density/Resistivity and Sonic Transit Time/Resistivity Crossplots," The American Association of Petroleum Geologists Bulletin, Feb. 1984, 68(2):121-129, 9 pages.
Min et al., "Wollastonite carbonation in water-bearing supercritical CO2: Effects of water saturation conditions, temperature, and pressure," Chemical Geology, Apr. 2018, 483:239-246, 35 pages.
Mishra et al., "Micro Porosity within the Organic Matter and its Impact on Assessment of Unconventional Potential of a Kerogen Rich Najmah Formation in Kuwait," SPE-197507-MS, Abu Dhabi International Petroleum Exhibition & Conference, OnePetro, 2019, 14 pages.
Nie et al., "Probing Single Molecules and Single Nanoparticles by Surface-Enhanced Raman Scattering," Science, Feb. 21, 1997, 275(5303):1102-1106, 6 pages.
Nottenburg et al., "Temperature and stress dependence of electrical and mechanical properties of Green River oil shale," Fuel, Feb. 1979, 58(2):144-148, 5 pages.
Panahi et al., "A 4D synchrotron X-ray tomography study of the formation of hydrocarbon migration pathways in heated organic-rich shale," SPE Journal, Apr. 2013, 366-377, 12 pages.
Pearce et al., "SO2 impurity impacts on experimental and simulated CO2-water-reservoir rock reactions at carbon storage conditions," Chemical Geology, Apr. 2015, 399:65-86, 22 pages.
Pollock et al., "Micro-thermal analysis: techniques and applications," Journal of Physics D: Applied Physics, 2001, 34(9):R23-R53, 31 pages.
Ponomarev et al., "Tomography in Geology: 3D Modeling and Analysis of Structural Features of Rocks Using Computed Micro-Tomography," IOP Conf. Ser.: Mater. Sci. Eng., Oct. 1, 2016, 154(012030):1-6, 6 pages.
Radiologycafe.com [online], "CT equipment," Available on or before Jun. 13, 2021, retrieved on Dec. 26, 2023, URL <https://www.radiologycafe.com/frcr-physicsnotes/ct-imaging/ct-equipment/>, 10 pages.
Radiopaedia.org [online], "Image reconstruction (CT)," Available on or before Jun. 29, 2019, Internet Archive: Wayback Machine URL<http://web.archive.org/web/20190629013455/https://radiopaedia.org/articles/image-reconstruction-ct?lang=us>, Retrieved on Dec. 26, 2023, URL <https://radiopaedia.org/articles/image-reconstruction-ct?lang=us>, 7 pages.
Rashadan et al., "Effect of the Preparation Route, PEG and Annealing on the Phase Stability of Fe3O4 Nanoparticles and Their Magnetic Properties," Journal of Experimental Nanoscience, Aug. 4, 2011, 8(2):210-222, 14 pages.
Rodriguez et al., "Imaging Techniques for Analyzing Shale Pores and Minerals," NETL-TRS-Jun. 2014, Dec. 2, 2014, 44 pages.
Saif et al., "Dynamic imaging of oil shale pyrolysis using synchrotron X-ray microtomography," Geophysical Research Letters, Jul. 2, 2016, 43:6799-6807, 9 pages.
Saif et al., "Microstructural imaging and characterization of oil shale before and after pyrolysis," Fuel, Jun. 1, 2017, 197:562-574, 13 pages.
Saif et al., "Multi-scale multi-dimensional microstructure imaging of oil shale pyrolysis using X-ray micro-tomography, automated ultra-high resolution SEM, MAPS Mineralogy and FIB-SEM," Applied Energy, Sep. 15, 2017, 202:628-647, 20 pages.
Sanei, "Genesis of solid bitumen," Scientific Reports, 2020, 10(1):1-10, 10 pages.
Saxena et al., "Rock properties from micro-CT images: Digital rock transforms for resolution, pore vol. and field of view," Advances in Water Resources, Dec. 2019, 134(103419):1-13, 13 pages.
Schlüter et al., "Image processing of multiphase images obtained via X-ray microtomography: a review," Water Resources Research 2014, 50(4):3615-3639, 70 pages.
Shabro et al., "Pore-scaling modeling of electrical resistivity and permeability in FIB-SEM images of organic mudrock," presented at the SPWLA 54th Annual Logging Symposium, New Orleans, Louisiana, Jun. 22-26, 2013, 13 pages.
Shukla et al., "Nanoindentation Studies on Shales," presented at the 47th US Rock Mechanics/Geomechanics Symposium, San Francisco, California, Jun. 23-26, 2013, 10 pages.
Sinha, "Surface Area Study in Organic Rich Shales using Nitrogen Adsorption," thesis submitted to the Graduate Faculty in partial fulfillment of the requirements for the degree of Master of Science, 2017, 144 pages.
Solomon et al., "Synthesis and Study of Silver Nanoparticles," Journal of Chemical Education, Feb. 2007, 84(2):322-325, 4 pages.
Stiles et al., "Surface-Enhanced Raman Spectroscopy," Annual Review of Analytical Chemistry, Mar. 18, 2008, 1(1):601-626, 29 pages.
Tabatabaei et al., "Well performance diagnosis with temperature profile measurements," in SPE Annual Technical Conference and Exhibition, Society of Petroleum Engineers, Oct. 30-Nov. 2, 2011, 16 pages.
Tathed et al., "Hydrocarbon saturation in Bakken Petroleum System based on joint inversion of resistivity and dielectric dispersion logs," Fuel, Dec. 2018, 233:45-55, 11 pages.
Trippetta et al., "The seismic signature of heavy oil on carbonate reservoir through laboratory experiments and AVA modelling, " Journal of Petroleum Science and Engineering, 2019, 177:849-860, 12 pages.
Tu et al., "Development of LabVIEW Based Micro Computed Tomography System on Vertical Rotary Gantry," IFMBE Proceedings, Jan. 2015, 45:273-276, 4 pages.
Van Lieshout et al., "Programmed-temperature vaporiser injector as a new analytical tool for combined thermal desorption-pyrolysis of solid samples Application to geochemical analysis," Journal of Chromatography A, Mar. 1997, 764(1):73-84, 12 pages.
Wang et al., "Characterization of electrical properties of organic-rich shales at nano/micro scales," Marine and Petroleum Geology, Jun. 2017, 86:563-572, 10 pages.
Wildenschild et al., "X-ray imaging and analysis techniques for quantifying pore-scale structure and processes in subsurface porous medium systems," Advances in Water Resources, Jan. 2013, 51:217-246, 30 pages.
Wu et al., "An experimental study of organic matter, minerals and porosity evolution in shales within high-temperature and high-pressure constraints," Marine and Petroleum Geology, Apr. 2019, 102:377-390, 14 pages.
Yang et al., "Nanoscale geochemical and geomechanical characterization of organic matter in shale," Nature Communications, Dec. 19, 2017, 8(2179):1-9, 9 pages.
Yang et al., "In situ catalytic fast pyrolysis of lignin over biochar and activated carbon derived from the identical process," Fuel Processing Technology, Dec. 2021, 227:107103, 13 pages.
Yoksoulian et al., "Mineralogical alterations during laboratory-scale carbon sequestration experiments for the Illinois Basin," Energy Procedia, 2013, 37:5601-5611, 11 pages.

* cited by examiner

ANALYSIS OF SOURCE ROCKS IN PYROLYSIS EXPERIMENTS

TECHNICAL FIELD

This disclosure relates generally to systems and methods to evaluate a source rock sample from a subterranean reservoir.

BACKGROUND

Petroleum potential of subterranean sources can be evaluated using various laboratory methods. Hydrous pyrolysis utilizes a sealed chamber to subject a rock sample to a controlled pressure and temperature environment under aqueous conditions simulating the natural conditions of the source rock. This technique can be used to simulate the natural generation of petroleum fluid from organic-rich source rocks.

SUMMARY

Certain aspects of the subject matter herein can be implemented as an apparatus. The apparatus includes a pyrolysis chamber with a floor and walls defining an interior space and a removable head. The pyrolysis chamber is configured to receive and hold within the interior space a volume of an aqueous fluid and to maintain a pressure within the interior space for a duration of an experimental period when the removable head is in a closed position. The apparatus further includes a heater configured to heat the fluid when the fluid is present in the interior space for the duration of the experimental period and a sample basket assembly comprising a plurality of baskets attached to the removable head by one or more rods. Each basket is configured to receive one or more source rock samples. The sample basket assembly is configured such that, when the removable head is in the closed position and the one or more source samples are disposed within each basket, the one or more samples are for the duration of the experimental period suspended in a substantially stationary position above the floor while permitting contact of the one or more source samples with the aqueous fluid, and removal of the removable head from the pyrolysis chamber upon completion of the experimental period removes the plurality of baskets from the interior space such that the one or more samples can be retrieved from the plurality of baskets.

Certain aspects of the subject matter herein can be implemented as a method. The method includes determining a physical or chemical characteristic of a first source rock sample by individually imaging, as a first imaging instance, the first source rock sample and, after the first imaging instance, disposing the first source rock sample in a first basket of a sample basket assembly, the sample basket assembly attached by one or more rods to a removable head of a pyrolysis chamber of a pyrolysis apparatus, the pyrolysis chamber comprising a floor and walls defining an interior space. The method further includes determining a physical or chemical characteristic of second source rock sample by individually imaging, as a second imaging instance, the first source rock sample and, after the second imaging instance, disposing the second source rock sample in a second basket of the sample basket assembly. The method further includes at least partially filling the interior space with a volume of an aqueous fluid and attaching the removable head to the pyrolysis chamber, thereby suspending the first source rock sample and the second source rock sample in the interior space in a position above the floor. With the removable head in the closed position, a pressure and heat are applied to the interior space for a duration of an experimental period. The sample basket assembly affixes the first source rock sample and the second rock sample substantially stationary in the position for the duration of the experimental period while permitting contact of the first source rock sample and the second rock sample with the aqueous fluid. The method further includes, after the experimental period, detaching the removable head from the pyrolysis chamber. After the detaching, the first source rock sample and the second source rock sample are retrieved from the first basket and the second basket, respectively. The method further includes individually imaging, as a third imaging instance, the first source rock sample to determine a change in the physical or chemical characteristic of the first source rock sample, and individually imaging, as a fourth imaging instance, the second source rock sample to determine a change in the physical or chemical characteristic of the second source rock sample.

DETAILED DESCRIPTION

Figures 1A, 1B:
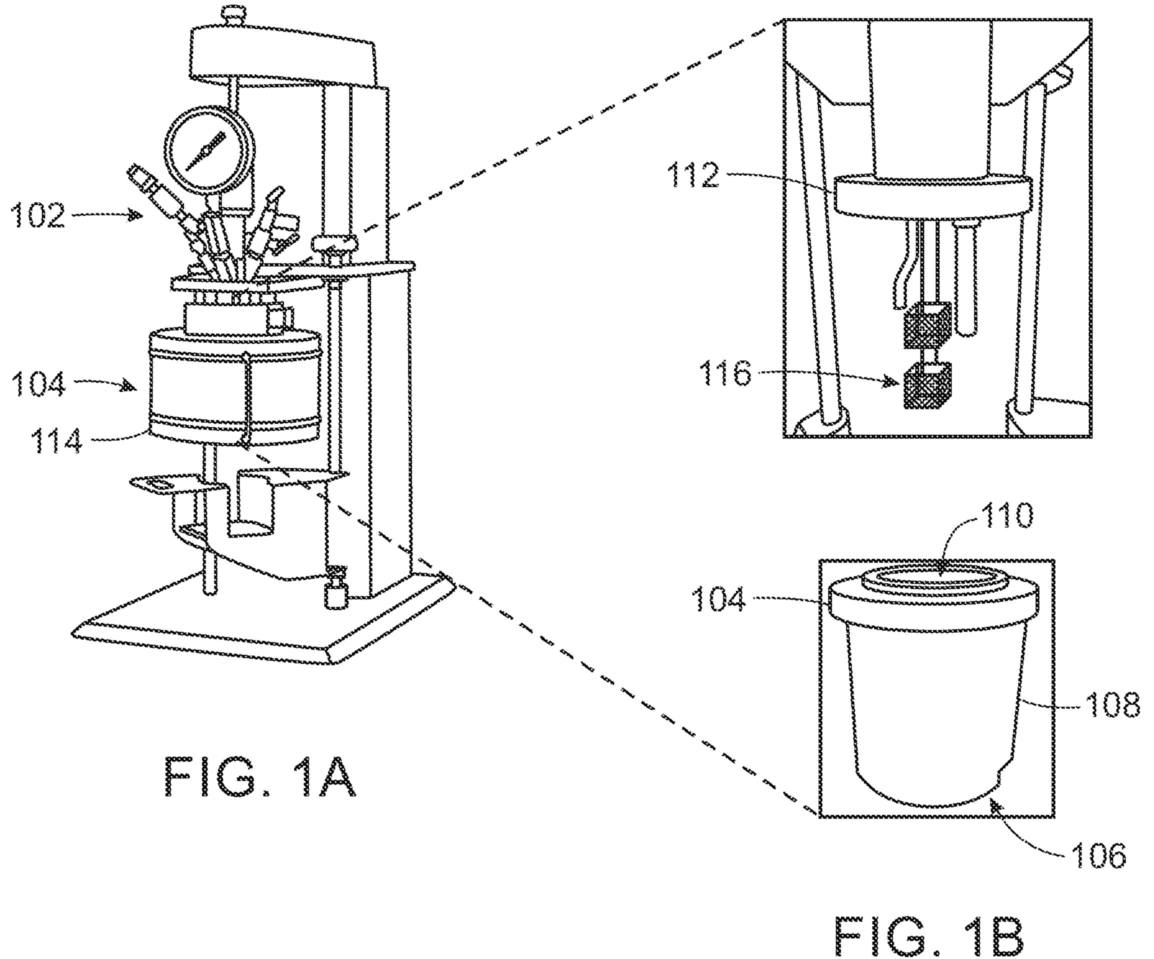
FIGS. 1A and 1B are schematic illustrations of an apparatus for conducting pyrolysis experiments in accordance with embodiments of the present disclosure.

High temperature, high pressure batch reaction experiments are used for various geological applications, including, but not limited to, petroleum generation, carbon sequestration, and subsurface hydrogen storage. Hydrous pyrolysis is one type of experiment that can be performed in such a reactor, and this technique is used to simulate the natural generation of petroleum-like products from source rocks. Hydrous pyrolysis generates bitumen and expelled oil from an organic-rich source rock through temperature-controlled experiments in the presence of water. Typical experiments are run between 270-365° C. and last for 72 hours. If running kinetic studies, the time interval can vary between ~12-300 hours. The goal of using this technique is to artificially mature a source rock from the immature window up to the gas maturity window. At each heating stage, expelled oil and the remaining source rock are analyzed to ascertain maturity and compositional differences. This type of data can be used as input parameters in basin models, helping scientists understand how oil is generated from a source rock in a basin, and what areas should be drilled next during exploration initiatives.

Analytical data can be acquired before and after each experiment, enabling correlations between the original immature source rock and the subsequent artificially heated sample. Maturity and compositional differences obtained before and after the reactor experiments are typically acquired using analytical instruments like a gas chromatograph (GC) and gas chromatograph mass spectrometer (GCMS). However, these instruments can only analyze oils and soluble bitumen that have been extracted using solvents. Obtaining maturity, compositional, and physical data through visual techniques (e.g., microspectrophotometer, petrographic microscope, scanning electron microscope, etc.) can be quite difficult to achieve. This is due to the simple design of the reactor vessel. In most reactor experiments, source rocks are initially crushed to grain sizes between 0.5-2 cm. These rock chips are then mixed with deionized water and merely placed loosely inside of the vessel for the experiments. Because the rock chips can move around the vessel during the experiments and when subsequent retrieval is attempted, it is nearly impossible to image the same rock chip before and after the experiment. Therefore, obtaining data on parameters like pore size distribution, permeability, fracturing, and elemental distributions can be difficult or impossible to achieve. While thermoplastic or glass liners have been designed to hold and contain the rock chips and water at the bottom of the reactor vessel, the extreme pressure and temperature of typical pyrolysis experiments can oxidize and disintegrate the liners. Furthermore, rock samples held either loosely in the chamber or held in liners at the bottom or sides of a chamber can stick to the liners or chamber walls, causing uneven circulation of fluids around the samples during pyrolysis and potentially causing fracturing and other damage to the samples when removal from the chamber is attempted.

In accordance with an embodiment of the present disclosure, an improved apparatus and method for sample management and analysis is disclosed. The apparatus utilizes a sample basket assembly using a plurality of individual baskets comprised of a metallic alloy resistant to high temperatures and pressures. In this way, data be acquired using geochemical techniques for the hydrocarbons expelled from the rock samples and also using imagery techniques for the individual rock samples themselves (e.g., for changes in physical and chemical characteristics of the source rock samples themselves such as maturity, compositional differences of organic matter, porosity, fractures, and elemental distributions). Because the samples are held individually in a proper static position in the baskets and individually retrieved, the user can ensure that the comparisons of experimental data before and after pyrolysis are made using same individual samples. This integration of data can aid in fully understanding how oil is generated in a source rock for basin modeling applications.

FIGS. 1A and 1B are schematic illustrations of an apparatus for conducting pyrolysis experiments in accordance with embodiments of the present disclosure. Apparatus 102 includes a pyrolysis chamber 104 which in turn includes a floor 106 and walls 108. In some embodiments, the floor and walls are separate components joined together; in other embodiments, the floor and walls are a single component. Floor 106 and walls 108 in turn define an interior space 110. Interior space 110 can be enclosed by attaching removable head 112 (for example, with a threaded connection) to form a pressure seal. A sample basket assembly 116 is attached to removable head 112, and is described in greater detail in FIGS. 2A-2B and FIG. 3.

Apparatus 102 further includes a heater 114 configured to heat fluid in the interior space 110 when the fluid is present in the interior space for the duration of the experimental period. Apparatus 102 can further include one or more pressure inlets and outlets, and various sensors, gauges, and meters for sensing and displaying the temperature, pressure, and other parameters within interior space 110 and in connection with other aspects of the apparatus. When the removable head is attached and a seal is formed, the apparatus is configured to hold within the interior space 110 a volume of an aqueous fluid and to maintain a desired pressure and temperature within the interior space for a duration of a pyrolysis experiment.

Figure 2A:
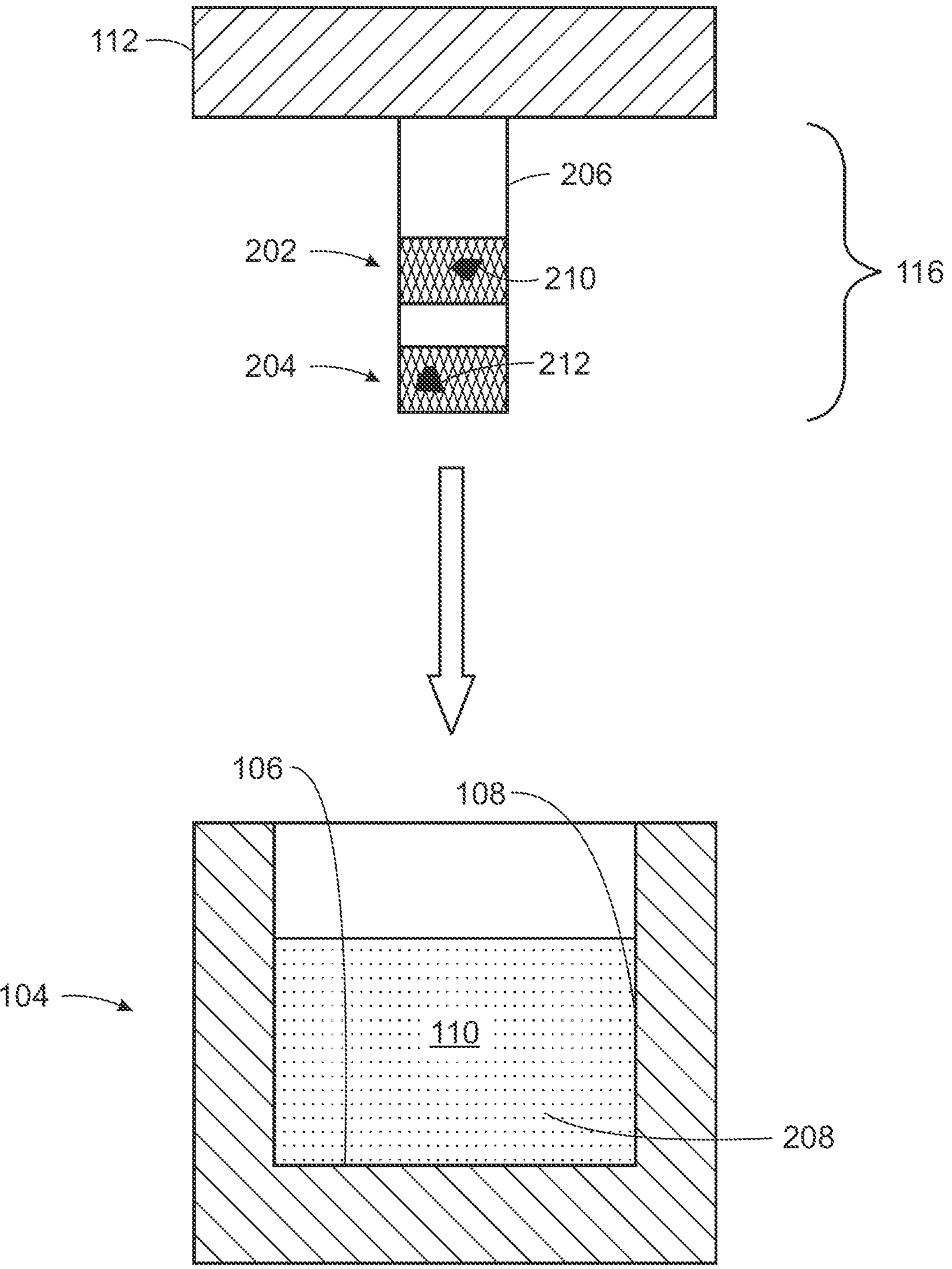
FIGS. 2A and 2B are schematic illustrations showing greater detail of a sample basket assembly and its configuration when a removable head is in its open and closed configuration with respect to a pyrolysis chamber in accordance with embodiments of the present disclosure.
Figure 2B:
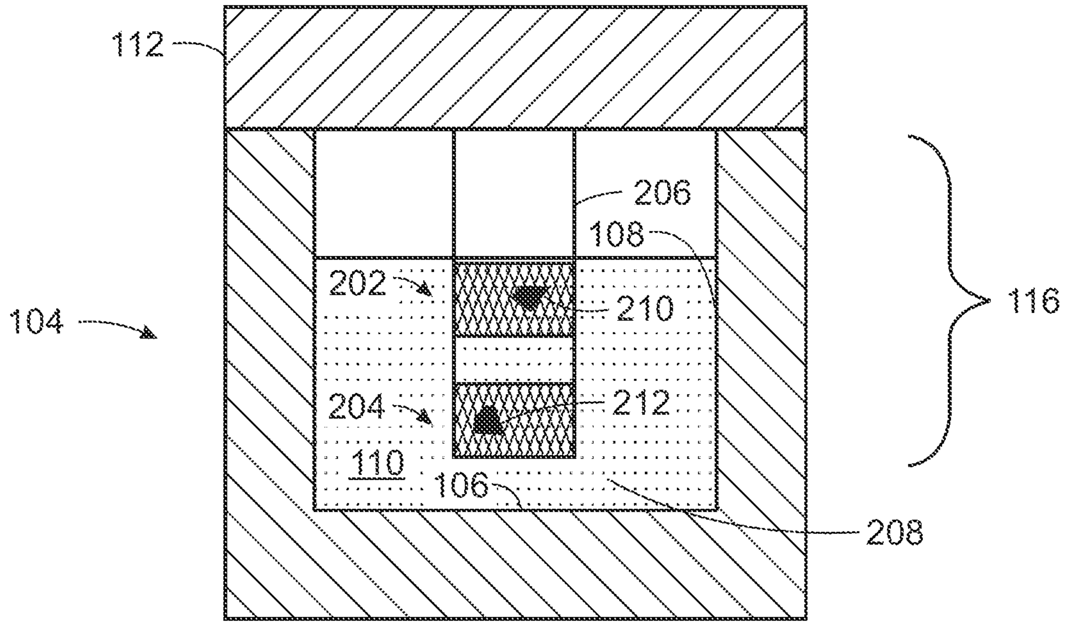

FIGS. 2A and 2B are schematic illustrations showing greater detail of sample basket assembly 116 and its configuration when removable head 112 is in its open and closed configurations in accordance with embodiments of the present disclosure. In the illustrated embodiment, sample basket assembly 116 includes a first metallic basket 202 and a second metallic basket 204. In some embodiments a sample basket assembly can include a greater or lesser number of baskets. Baskets 202 and 204 are attached to removable head 112 by one or more rods 206, each metallic basket configured to such that each one or more source rock samples (for example, samples 210 and 212) can be readily disposed within the baskets when removable head 112 is not attached to chamber 104 (FIG. 2A). When the removable head is in the closed position (FIG. 2B) the basket assembly ensures that the samples, for the duration of the experimental period, are suspended in a substantially stationary position above the floor within interior space 110. An aqueous fluid 208 (for example, an aqueous liquid) can be placed within interior space 110. During the pyrolysis experiment, the temperature in the interior space 110 can be high enough (for example, approximately 270 degrees or greater) to partially or completely vaporize aqueous fluid 208. Upon completion of the experiment, removal of the removable head 112 from the pyrolysis chamber removes the plurality of metallic baskets from the interior space such that the one or more samples can be readily retrieved from the plurality of metallic baskets.

Figure 3:
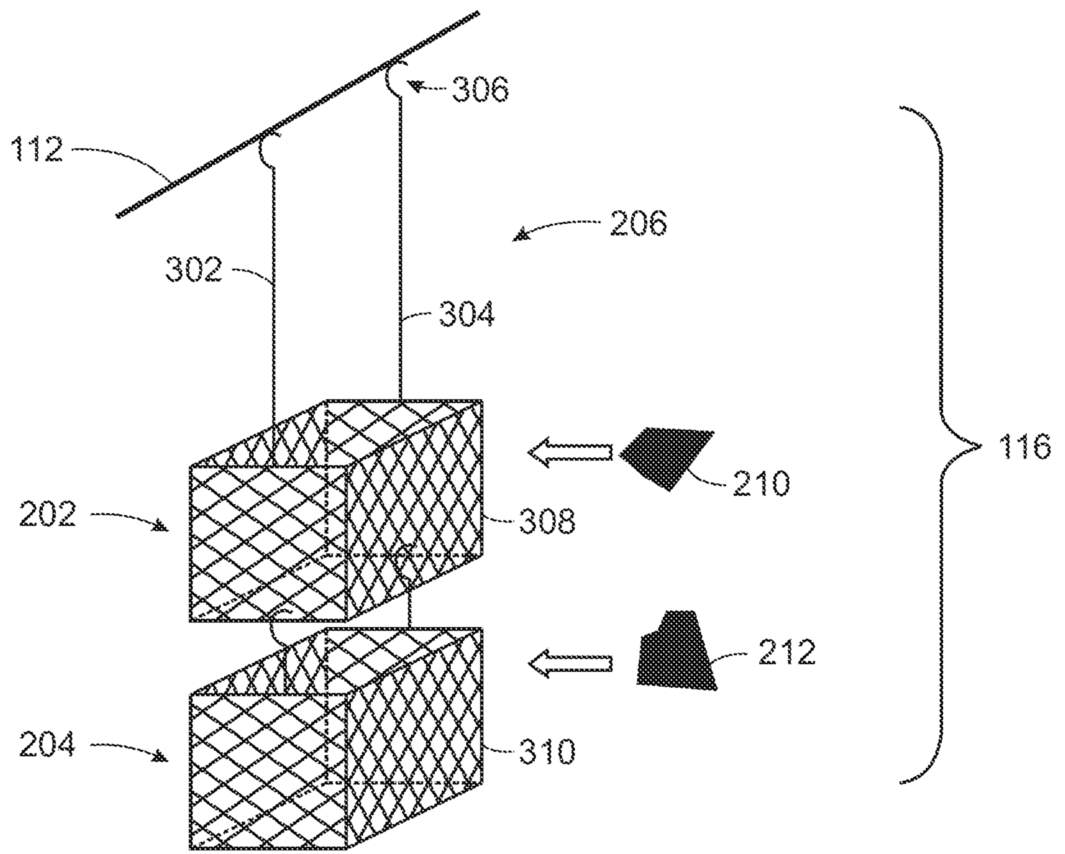
FIG. 3 is a schematic illustration showing a sample basket assembly in greater detail in accordance with embodiments of the present disclosure.

FIG. 3 is a schematic illustration showing sample basket assembly 116 in greater detail in accordance with embodiments of the present disclosure. In the illustrated embodiment, wherein the rods 206 comprise a pair of rods 302 and 304. Rods 302 and 304 are attached at their respective ends to removable head 112 by, for example, a hook 306 or other suitable attachment. The other ends of rods 302 and 304 are attached to the sample baskets 202 and 204. More specifically, in the illustrated embodiment, rod 302 is attached to one side of baskets 202 and 204 is attached to the other side of sample baskets 202 and 204.

In some embodiments, rods 302 and 304 are flexible wires; in other embodiments, rods 302 and 304 are rigid rods. Baskets 202 and 204 and rods 302 and 304 in some embodiments are made of a nickel-chromium-molybdenum alloy such as Hastelloy C276 (UNS N10276), which can withstand temperatures up to 1600° C. and is resistant to corrosion that can occur within a pressure vessel when conducting pyrolysis experiments, particularly when such experiments include high-sulfur source rocks that can generate $H_2S$, which acidifies water and causes corrosion to metals such as carbon steels.

The wire gridding of the baskets can be large enough to allow the aqueous fluid (liquid or vapor) to flow through and be in contact with the samples during the experiment, while being small enough that no sample or sample pieces can fall out of the basket. In some embodiments, the baskets are sized (and otherwise configured) such that a rock sample disposed therein that has been cut (sized) for a sample holder of an imaging apparatus (such as an SEM) is held substantially immobilized relative to the removable head. By holding the sample substantially immobile relative to the removable head during the experiment and also as the head is attached to and detached from the chamber, fracturing or other damage to the sample can be reduced or eliminated, and no further cutting or dimensioning of the sample is necessary before the sample is placed into the imaging apparatus sample holder. For example, insertion of a sample into an SEM imaging apparatus may require that the sample be cut to approximately 1 cm (length) by 1 cm (width) by 0.25 cm (height). In order to hold such a sample immobile in the basket, the basket can have dimensions of approximately 1.5 cm×1.5 cm×1.5 cm with gridding approximately 3 mm wide. The baskets can include doors 308 and 310 which can be open so that samples (for example, samples 210 and 212) can be easily placed inside the individual respective baskets and the doors closed to aid in immobilizing the samples within the basket. Although FIG. 3 shows two baskets, each attached to a pair of rods and each holding one sample, in other embodiments a sample assembly can include a different number of baskets, one or more of which may hold one (or more than one) sample, and a greater or lesser number of rods. For example, a basket assembly in some embodiments can include three baskets, each configured to hold a respective group of two or more rock samples. In some embodiments, in addition to the samples held in the baskets, some samples can be placed loosely in the chamber.

Figure 4:
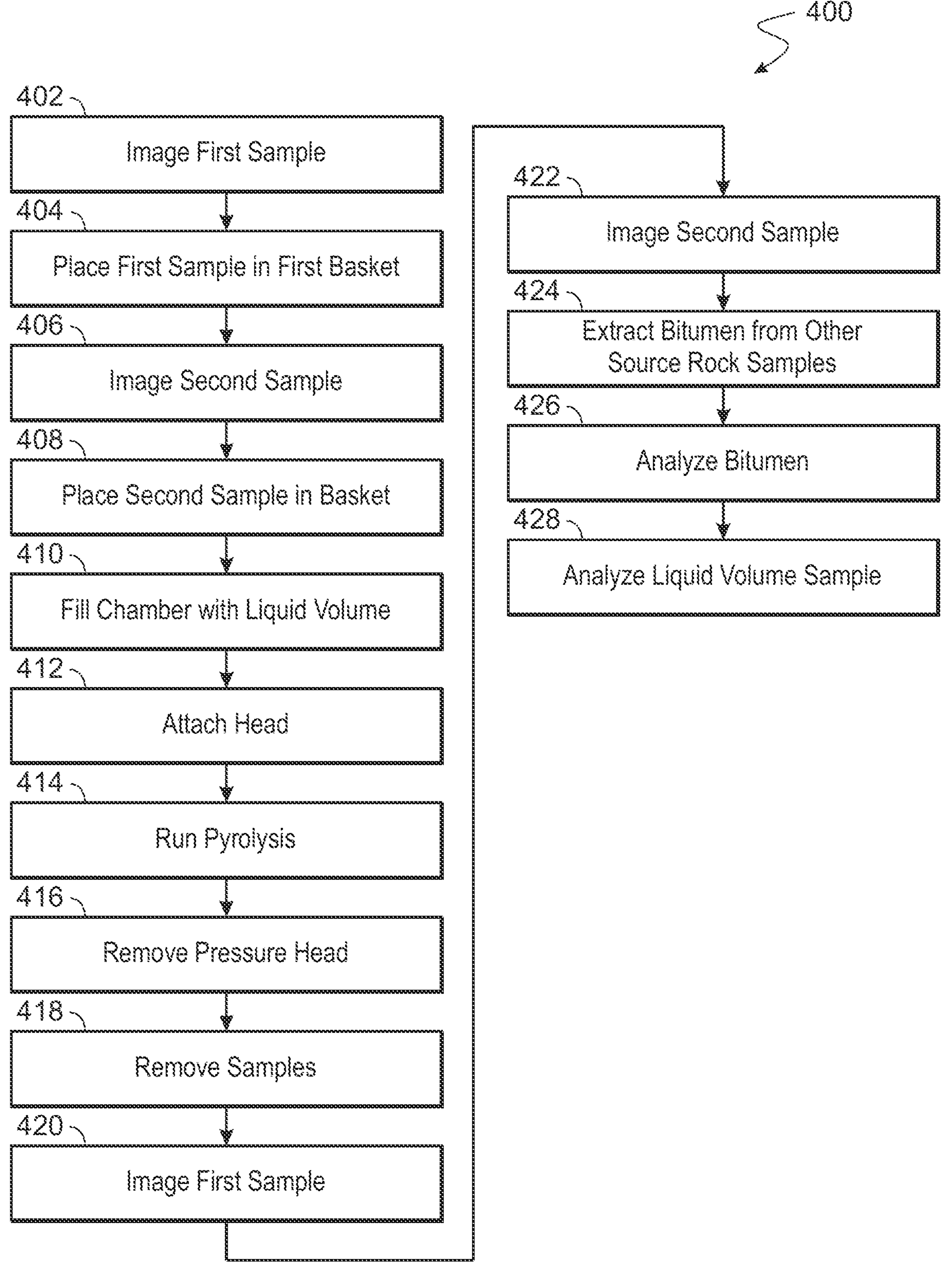
FIG. 4 is a process flow diagram of a method 400 of analyzing source rocks for petroleum potential and other related geochemical characteristics in accordance with embodiments of the present disclosure.

FIG. 4 is a process flow diagram of a method 400 of analyzing source rocks for petroleum potential and other related geochemical characteristics in accordance with embodiments of the present disclosure. Method 400 will be described in reference to system 100 described in reference to the above figures. The method begins at step 402 in which one or more physical or chemical characteristics of an individual source rock sample are determined using scanning electron microscopy (SEM), petrographic microscopy, micro-spectrophotometry, or other suitable imaging technique. The physical or chemical characteristics can include, for example, maturity, composition, or other characteristics. In preparation for the imaging, rock can be cut with a diamond saw and ion-milled such that they are a suitable size and shape for the imaging apparatus and for placement in a sample basket. For example, in some embodiments, if a sample basket is approximately 1.45 cm in length and width, a sample can be cut to approximately 1 cm (length) by 1 cm (width) by 0.25 cm (height). In some embodiments, the sample can be etched to distinguish it from other rock samples used in the experiment and to aid in for consistent orientation in the imaging apparatus for imaging before and after a pyrolysis experiment.

Proceeding to step 404, the sample can be placed in one of the sample baskets of the sample basket assembly. At step 406, sample preparation and imaging can similarly be conducted on a second sample that, at step 408, can be placed in another of the sample baskets of the sample basket assembly. In some embodiments, one sample is disposed in each basket. In some embodiments, a greater number of samples (for example, two or three or more) are disposed in one or both baskets. In some embodiments, a sample basket assembly can include a greater number of baskets (for example, three baskets). In some embodiments, a sample basket assembly has only one basket (such that steps 406 and 408 can be omitted).

At step 410, a volume of an aqueous liquid such as deionized water is added to the interior space of the pyrolysis chamber, at least partially filling it. In some embodiments, the volume or aqueous liquid is approximately 30 to 40 milliliters. Proceeding to step 412, the removable head is attached to the pyrolysis chamber, such that the source rock samples are suspended and held in a stationary position above the floor within the chamber. In some embodiments, at this step, in addition to the rock samples in the baskets, additional rock samples are also placed loosely in the interior space (not in the baskets). In some embodiments, the total weight of all of rock samples combined can be approximately 30 grams.

Proceeding to step 414, with the removable head in the closed position and scaled, pressure and heat are applied to the interior space for a duration of the pyrolysis portion of the experiment. The sample basket assembly suspended by the rods affixes the first source rock sample and the second rock sample substantially stationary in the position for the duration, away from the sides and floor of the chamber of the experimental period. An experimental run can have, for example a duration of 12 to 300 hours at a temperature of 270-365° C.). Some runs can be for a greater or lesser time at a greater or lesser temperature. In some runs, the pressure and/or temperature are varied during the run.

Proceeding to step 416, after the experimental period, after the allotted time of the pyrolysis run has been completed for its full duration, the chamber is allowed to cool to room temperature and the removable head is removed from the chamber, allowing easy access to the baskets and allowing for the rock samples to be individually retrieved. At step 418, after removal from the baskets, the samples can be washed with toluene (or another aromatic solvent) to remove any oil that is adsorbed to the surface of the rock pieces. This adsorbed oil can be analyzed by geochemical instruments such as a gas chromatograph and gas chromatograph mass spectrometer. The samples can be placed onto sample holders (or into epoxy plugs) for imaging using the same imaging techniques and apparatus as before the pyrolysis run (for example, SEM, petrographic microscope, and/or microspectrophotometer) to determine any changes caused by the pyrolysis run in the physical or chemical characteristics of the samples. In some embodiments, the rock samples can be etched prior to placement in the baskets, such that the samples can be placed in the imaging apparatus in the same orientation as the pre-pyrolysis imaging, further enabling accurate and precise comparisons.

In some embodiments, the method proceeds to step 424 in which the remaining rock pieces can undergo solvent extraction using dichloromethane (or an equivalent solvent) to remove soluble bitumen. The solvent-extracted bitumen can at step 426 be analyzed by geochemical instruments such as a GC and GCMS. Similarly, at step 427, any hydrocarbons expelled from the samples into the surrounding liquid can be removed with a pipette and likewise geochemically analyzed using GC, GCMS, or other suitable techniques.

In this disclosure, "approximately" or "substantially" mean a deviation or allowance of up to 10 percent (%) and any variation from a mentioned value is within the tolerance limits of any machinery used to manufacture the part. Likewise, "about" can also allow for a degree of variability in a value or range, for example, within 10%, within 5%, or within 1% of a stated value or of a stated limit of a range.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement “X to Y” has the same meaning as “about X to about Y,” unless indicated otherwise. Likewise, the statement “X, Y, or Z” has the same meaning as “about X, about Y, or about Z,” unless indicated otherwise.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

EXAMPLES

In a first aspect, an apparatus includes a pyrolysis chamber with a floor and walls defining an interior space and a removable head. The pyrolysis chamber is configured to receive and hold within the interior space a volume of an aqueous fluid and to maintain a pressure within the interior space for a duration of an experimental period when the removable head is in a closed position. The apparatus further includes a heater configured to heat the fluid when the fluid is present in the interior space for the duration of the experimental period and a sample basket assembly comprising a plurality of baskets attached to the removable head by one or more rods. Each basket is configured to receive one or more source rock samples. The sample basket assembly is configured such that, when the removable head is in the closed position and the one or more source samples are disposed within each basket, the one or more samples are for the duration of the experimental period suspended in a substantially stationary position above the floor while permitting contact of the one or more source samples with the aqueous fluid, and removal of the removable head from the pyrolysis chamber upon completion of the experimental period removes the plurality of baskets from the interior space such that the one or more samples can be retrieved from the plurality of baskets.

In a second aspect in accordance with the first aspect, each basket of the plurality of baskets is a metallic basket.

In a third aspect in accordance with the first or second aspects, each basket of the plurality of baskets comprise nickel-chromium-molybdenum alloy.

In a fourth aspect in accordance with any of the first to third aspects, the one or more rods comprise nickel-chromium-molybdenum alloy.

In a fifth aspect in accordance with any of the first to fourth aspects, the one or more rods comprise metal wires.

In a sixth aspect in accordance with any of the first to fifth aspects, the one or more rods comprise rigid metal rods.

In a seventh aspect in accordance with any of the first to sixth aspects, the one or more rods comprise a pair of rods, and wherein a first end of a first rod of the pair of rods and a first end of a second rod of the pair of rods are attached to the removable head and a second end of the first rod of the pair of rods is attached to a first side of a first basket of the plurality of baskets and a second end of the second rod of the pair of rods is attached to a second side of the first basket of the plurality of baskets.

In an eighth aspect in accordance with any of the first to seventh aspects, at least one basket of the plurality of baskets is dimensioned such that a sample sized for a sample holder of an imaging apparatus is substantially immobilized relative to the removable head if the sample sized for the sample holder is disposed within the at least one basket.

In a ninth aspect in accordance with any of the first to eighth aspects, the sample holder of the imaging apparatus is configured to hold a sample of approximately 1 cm by 1 cm by 0.25 cm and the at least one basket is approximately 1.5 cm×1.5 cm×1.5 cm.

In a tenth aspect, a method includes determining a physical or chemical characteristic of a first source rock sample by individually imaging, as a first imaging instance, the first source rock sample and, after the first imaging instance, disposing the first source rock sample in a first basket of a sample basket assembly, the sample basket assembly attached by one or more rods to a removable head of a pyrolysis chamber of a pyrolysis apparatus, the pyrolysis chamber comprising a floor and walls defining an interior space. The method further includes determining a physical or chemical characteristic of second source rock sample by individually imaging, as a second imaging instance, the first source rock sample and, after the second imaging instance, disposing the second source rock sample in a second basket of the sample basket assembly. The method further includes at least partially filling the interior space with a volume of an aqueous fluid and attaching the removable head to the pyrolysis chamber, thereby suspending the first source rock sample and the second source rock sample in the interior space in a position above the floor. With the removable head in the closed position, a pressure and heat are applied to the interior space for a duration of an experimental period. The sample basket assembly affixes the first source rock sample and the second rock sample substantially stationary in the position for the duration of the experimental period while permitting contact of the first source rock sample and the second rock sample with the aqueous fluid. The method further includes, after the experimental period, detaching the removable head from the pyrolysis chamber. After the detaching, the first source rock sample and the second source rock sample are retrieved from the first basket and the second basket, respectively. The method further includes individually imaging, as a third imaging instance, the first source rock sample to determine a change in the physical or chemical characteristic of the first source rock sample, and individually imaging, as a fourth imaging instance, the second source rock sample to determine a change in the physical or chemical characteristic of the second source rock sample.

In an eleventh aspect in accordance with the tenth aspect, at least the first imaging instance and the third imaging instance of the imaging instances comprises imaging with an SEM apparatus.

In a twelfth aspect in accordance with the tenth or eleventh aspects, at least one of the imaging instances comprises imaging with a petrographic microscope.

In a thirteenth aspect in accordance with any of the tenth to eleventh aspects, at least one of the imaging instances comprises imaging with microspectrophotometer.

In a fourteenth aspect in accordance with any of the tenth to thirteenth aspects, the method further includes, before the first imaging instance, etching a pattern in the first source rock, and wherein the first imaging instance and the third imaging instance comprise orienting the first rock sample in a sample holder of an imaging apparatus based in part on the etched pattern.

In a fifteenth aspect in accordance with any of the tenth to fourteenth aspects, the method further includes, the experimental period, determining a geochemical characteristic of a hydrocarbon liquid expelled during the experimental period from one or more source rock samples disposed in the interior space.

In a sixteenth aspect in accordance with any of the tenth to fifteenth aspects, the determining the geochemical characteristic comprises analyzing the hydrocarbon liquid with a gas chromatograph.

In a seventeenth aspect in accordance with any of the tenth to sixteenth aspects, the first source rock sample and the second rock sample comprise two of three or more source rock samples disposed in the interior space for the duration of the experimental period, and further comprising, after the experimental period, extracting bitumen from one or more of the three or more source rock samples other than the first source rock sample and the second source rock sample.

In an eighteenth aspect in accordance with any of the tenth to seventeenth aspects, the plurality of baskets comprise nickel-chromium-molybdenum alloy.

In a nineteenth aspect in accordance with any of the tenth to eighteenth aspects, at least the first basket is dimensioned such that a sample sized for a sample holder of an imaging apparatus is substantially immobilized relative to the removable head if the sample sized for the sample holder is disposed within the first basket, and further comprising, before the first imaging instance, cutting the first source rock sample such that the first source rock sample is sized for the sample holder.

In a twentieth aspect in accordance with any of the tenth to nineteenth aspects, the sample holder of the imaging apparatus is configured to hold a sample of approximately 1 cm by 1 cm by 0.25 cm and the first basket is approximately 1.5 cm×1.5 cm×1.5 cm.

What is claimed is:

1. An apparatus comprising:

a pyrolysis chamber comprising a floor and walls defining an interior space and a removable head, the pyrolysis chamber configured to receive and hold within the interior space a volume of an aqueous fluid and to maintain a pressure within the interior space for a duration of an experimental period when the removable head is in a closed position;

a heater configured to heat the fluid when the fluid is present in the interior space for the duration of the experimental period; and a sample basket assembly comprising a plurality of baskets attached to the removable head by one or more rods, each basket configured to receive one or more source rock samples, the sample basket assembly configured such that:

when the removable head is in the closed position and the one or more source samples are disposed within each basket, the one or more samples are for the duration of the experimental period suspended in a substantially stationary position above the floor while permitting contact of the one or more source samples with the aqueous fluid; and removal of the removable head from the pyrolysis chamber upon completion of the experimental period removes the plurality of baskets from the interior space such that the one or more samples can be retrieved from the plurality of baskets.

2. The apparatus of claim 1, wherein each basket of the plurality of baskets is a metallic basket.

3. The apparatus of claim 1, wherein each basket of the plurality of baskets comprise nickel-chromium-molybdenum alloy.

4. The apparatus of claim 1, wherein the one or more rods comprise nickel-chromium-molybdenum alloy.

5. The apparatus of claim 1, wherein the one or more rods comprise metal wires.

6. The apparatus of claim 1, wherein the one or more rods comprise rigid metal rods.

7. The apparatus of claim 1, wherein the one or more rods comprise a pair of rods, and wherein a first end of a first rod of the pair of rods and a first end of a second rod of the pair of rods are attached to the removable head and a second end of the first rod of the pair of rods is attached to a first side of a first basket of the plurality of baskets and a second end of the second rod of the pair of rods is attached to a second side of the first basket of the plurality of baskets.

8. The apparatus of claim 1, wherein at least one basket of the plurality of baskets is dimensioned such that a sample sized for a sample holder of an imaging apparatus is substantially immobilized relative to the removable head if the sample sized for the sample holder is disposed within the at least one basket.

9. The apparatus of claim 8, wherein the sample holder of the imaging apparatus is configured to hold a sample of approximately 1 cm by 1 cm by 0.25 cm and the at least one basket is approximately 1.5 cm×1.5 cm×1.5 cm.

10. A method comprising:

determining a physical or chemical characteristic of a first source rock sample by individually imaging, as a first imaging instance, the first source rock sample;

after the first imaging instance, disposing the first source rock sample in a first basket of a sample basket assembly, the sample basket assembly attached by one or more rods to a removable head of a pyrolysis chamber of a pyrolysis apparatus, the pyrolysis chamber comprising a floor and walls defining an interior space;

determining a physical or chemical characteristic of second source rock sample by individually imaging, as a second imaging instance, the first source rock sample;

after the second imaging instance, disposing the second source rock sample in a second basket of the sample basket assembly;

at least partially filling the interior space with a volume of an aqueous fluid;

attaching the removable head to the pyrolysis chamber, thereby suspending the first source rock sample and the second source rock sample in the interior space in a position above the floor;

with the removable head in the closed position, applying a pressure and heat to the interior space for a duration of an experimental period, the sample basket assembly affixing the first source rock sample and the second rock sample substantially stationary in the position for the duration of the experimental period while permitting contact of the first source rock sample and the second rock sample with the aqueous fluid;

after the experimental period, detaching the removable head from the pyrolysis chamber; and after the detaching:

retrieving the first source rock sample and the second source rock sample from the first basket and the second basket, respectively;

individually imaging, as a third imaging instance, the first source rock sample to determine a change in the physical or chemical characteristic of the first source rock sample; and individually imaging, as a fourth imaging instance, the second source rock sample to determine a change in the physical or chemical characteristic of the second source rock sample.

11. The method of claim 10, wherein at least the first imaging instance and the third imaging instance of the imaging instances comprises imaging with an SEM apparatus.

12. The method of claim 10, wherein at least one of the imaging instances comprises imaging with a petrographic microscope.

13. The method of claim 10, wherein at least one of the imaging instances comprises imaging with microspectrophotometer.

14. The method of claim 10, further comprising, before the first imaging instance, etching a pattern in the first source rock, and wherein the first imaging instance and the third imaging instance comprise orienting the first rock sample in a sample holder of an imaging apparatus based in part on the etched pattern.

15. The method of claim 10, further comprising, after the experimental period, determining a geochemical characteristic of a hydrocarbon liquid expelled during the experimental period from one or more source rock samples disposed in the interior space.

16. The method of claim 15, wherein the determining the geochemical characteristic comprises analyzing the hydrocarbon liquid with a gas chromatograph.

17. The method of claim 10, wherein the first source rock sample and the second rock sample comprise two of three or more source rock samples disposed in the interior space for the duration of the experimental period, and further comprising, after the experimental period, extracting bitumen from one or more of the three or more source rock samples other than the first source rock sample and the second source rock sample.

18. The method of claim 10, wherein the plurality of baskets comprise nickel-chromium-molybdenum alloy.

19. The method of claim 10, wherein at least the first basket is dimensioned such that a sample sized for a sample holder of an imaging apparatus is substantially immobilized relative to the removable head if the sample sized for the sample holder is disposed within the first basket, and further comprising, before the first imaging instance, cutting the first source rock sample such that the first source rock sample is sized for the sample holder.

20. The method of claim 10, wherein the sample holder of the imaging apparatus is configured to hold a sample of approximately 1 cm by 1 cm by 0.25 cm and the first basket is approximately 1.5 cm×1.5 cm×1.5 cm.

* * * * *